(12) United States Patent
Kumar et al.

(10) Patent No.: US 6,376,683 B1
(45) Date of Patent: Apr. 23, 2002

(54) PROCESS FOR THE PREPARATION OF (4R, 6S)-4-HYDROXY-6-HYDROXYMETHYL-TETRAHYDROPYRAN-2-ONE

(75) Inventors: Pradeep Kumar; Rodney Agustinho Fernandes, both of Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/872,849

(22) Filed: Jun. 1, 2001

(51) Int. Cl.[7] .................... C07D 309/30; C07D 317/00

(52) U.S. Cl. .................. 549/292; 549/454; 549/430
(58) Field of Search ................... 549/292, 430, 549/454

*Primary Examiner*—Amelia Owens
(74) *Attorney, Agent, or Firm*—Schweitzer Cornman Gross & Bondell LLP

(57) ABSTRACT

The present invention relates to an improved, efficient and enantio-selective process for the synthesis of (4R, 6S)-4-hydroxy-6-hydroxymethyl tetrahydropyran-2-one, employing the Sharpless asymmetric dihydroxylation and regiospecific nucleophilic hydride opening of the cyclic sulfite/sulfate as the key steps. The invention also resides in the intermediates used in the process.

10 Claims, No Drawings

PROCESS FOR THE PREPARATION OF (4R, 6S)-4-HYDROXY-6-HYDROXYMETHYL-TETRAHYDROPYRAN-2-ONE

The present invention relates to an improved process for the preparation of (4R,6S)-4-hydroxy-6-hydroxymethyl tetrahydro-pyran-2-one of formula (1).

FORMULA-1

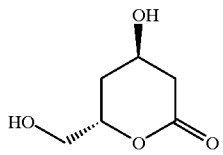

More particularly the present invention relates to the said process using (S)-(−)-Malic acid.

β-Hydroxy-δ-lactones are very important intermediates for the synthesis of a variety of hypocholesterolemic agents (cholesterol lowering drugs). Cholesterol biosynthesis inhibition has become a powerful tool to lower plasma cholesterol high levels. 3-Hydroxy-3-methyl-glutaryl Co-enzyme A (HMGCoA) reductase is a target of choice, because it is the early rate limiting step of the biosynthesis of cholesterol. Mevinolin [2] and Compactin [3] is a specific inhibitor of HMGCoA reductase and is effective in lowering blood plasma cholesterol levels (Endo, A. J. Med. Chem. 1985, 28, 401)

FORMULA -2

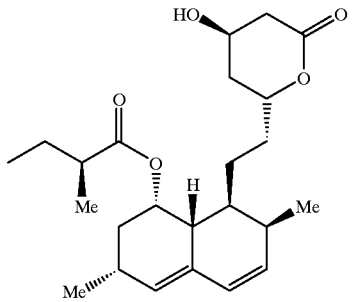

FORMULA -3

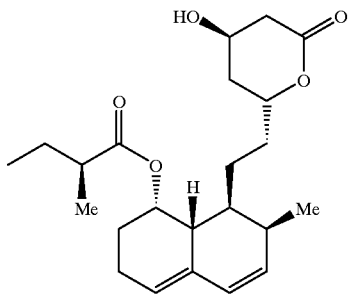

The important implications for treatment of coronary artery diseases have made these compounds the subject of intense research aimed at biological evaluation and chemical synthesis [Grieco, P. A.; Zelle, R. E.; Lis, R.; Finn, J. J. Am. Chem. Soc. 1983, 105, 1403). The key structural features in HMGCoA reductase inhibitors is the β-hydroxy-δ-lactone moiety that is the characteristic of this class of compounds known as mevinic acids which also contains a functionalised decalin unit connected to the lactone via an ethylene bridge. The biological activity is mainly due to the β-hydroxy-δ-lactone moiety and the role of decalin units is that of purely hydrophobic in nature.

In the prior-art, the synthesis of key pharmacophore β-hydroxy-δ-lactone segment of mevinic acid has been accomplished employing various synthetic strategies. A commonly used strategy for the incorporation of the lactone portion in the synthesis of both the natural materials and synthetic analogs is to employ the masked lactol which can be obtained from carbohydrate degradation (Prugh, J. D. et al Tet Lett 1982, 23, 281; Falck, J. R. Tet Lett 1982, 23, 4305; France, C. J. Tet Lett 1993, 34, 1635) as well as from L-malic acid (Clive D. L. J. Tet Lett 1984, 25, 2101; Guindon, Y. Tet Lett 1985, 26, 1185).

In another prior-art method, the lactone portion is obtained from tri-O-acetyl glucal, which can be derived from carbohydrates [Wareing, James R. (Sandoz, Inc., USA). U.S. Pat. No. 4,474,971, (1984)].

In another prior-art method, the derivatives of title compounds were prepared in 11 steps starting from 3β, 4α-dihydroxy 2α-(hydroxymethyl)-2,3-dihydro-2H-pyranyl triacetate [Jewell, C. F. et al. U.S. Pat. No. 4,625,039 (1986)].

In yet another prior-art method, the synthesis of mevinic acids as well as the synthetic analogs involves the coupling of aryl cuprates with chiral epoxy esters, which can be obtained from a variety of precursors.

In still another prior-art method, the epoxidation of α,β-unsaturated lactones followed by regioselective rupture of the oxirane rings is known to give the β-hydroxy adorned lactone fragment (Ogasawara, K. J. Chem. Soc. Chem. Commun 1989, 539; Ogasawara, K. et al. JP 11240877 (1999); Yadav V. K. I. J. Chem. 34 B, 1995, 1026) In yet another prior-art method, the kinetically controlled iodolactonisation and selenolactonisation strategies are known to give mevinic acid analogues (Bennett, F. et al. J C S Perkin Trans-I 1991, 133, 519 and 1543. Bennett, F. Tet Lett. 1988, 29, 4865).

In another prior-art method, the open chain precursors of the lactone moiety have been generated in optically active forms using chiral starting materials (Repic O, Tet. Lett 1984, 25, 2435), chiral auxiliaries (Lynch J. E. Tet. Lett. 1987, 28, 1385; Dittmer, D. C. J. Org. Chem 1994, 59, 4760) and also enzymatic biocatalyses (Torssell, K. Acta. Chem. Scand, 1977, B 31, 297; Bonini, C. J. Org. Chem. 1991, 4050).

In yet another prior-art method chiral as well as racemic analogs have been prepared using a hetero Diels-Alder reaction (Danishefsky et al al J. Am. Chem. Soc. 1982, 358, 104; Danishefsky, S. et al. J. Org. Chem. 1982, 47, 1981; Bauer, T. J. Chem. Soc. Chem. Comm. 1990, 1178).

Although, the lactone segment has been the target of an increasing number of synthetic efforts, their synthesis remains a challenge. Introduction of the required stereocentres at position C-4 and C-6 of the lactone is vital for the biological activity and has proved to be an important synthetic feature.

Some of the major drawbacks of the methods known in the prior-art are such as i) multi-step synthesis
ii) high cost of materials involved
iii) complicated reagents, longer reaction time and higher reaction temperature
iv) difficulties involved in the work-up procedures
v) difficulties involved in handling sophisticated reagents
vi) overall low yield of the desired lactone
vii) poor enantio- and diastereoselectivity
viii) lack of reusability of expensive reagents.

In view of the abovementioned drawbacks and disadvantages of the prior art processes, it is desirable to develop an improved, efficient and enantioselective process for the synthesis of (4R,6S)-4-hydroxy-6-hydroxymethyl tetrahydro-pyran-2-one.

The object of the present invention is to provide an improved, efficient and enantio-selective process for the synthesis of (4R,6S)4-hydroxy-6-hydroxymethyl tetrahydro-pyran-2-one, which overcomes the drawbacks of the prior-art processes employing the Sharpless asymmetric dihydroxylation and regiospecific nucleophilic hydride opening of the cyclic sulfite/sulfate as the key steps.

The significant feature of the present invention is:

i) The process relatively involves less number of steps.

ii) The reactions involved in each step, according to the present invention, could be carried out relatively at lower temperature or room temperature.

iii) The process leads to high yields of the desired products.

iv) All possible stereoisomers of the desired lactone could be prepared using this process.

v) The process gives high enantio-and diastereoselectivity of the products.

vi) The chiral ligands used to induce chirality could be recovered.

The process of the present invention is described in details in the schematic diagram herein below

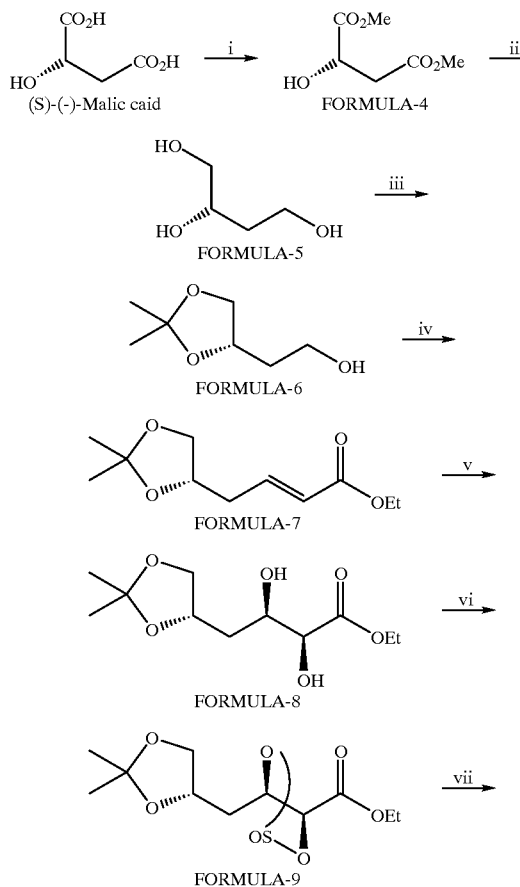

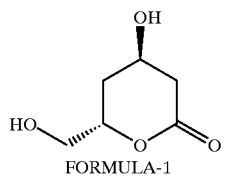

FORMULA-1

Accordingly, the present invention provides an improved, efficient and enantioselective process for the synthesis of (4R,6S)-4-hydroxy-6-hydroxymethyl tetrahydro-pyran-2-one which comprises i) reacting the (S)-(−)-Malic acid with a mixture of mineral acid and alcohol at room temperature for a period of 18 to 30 hrs to obtain the diester of (S)-(−)-Malic acid of formula (4)

ii) reducing the compound (4) with a hydride reducing reagent at room temperature to reflux temperature for a period of 8 to 12 hrs to obtain (S)-1,2,4-butanetriol of formula (5)

iii) treating the compound (5) with protecting reagent at room temperature for a period of 36 to 48 hrs to obtain (S)-1,2,4-butanetriol 1,2-acetonide of formula (6)

iv) oxidizing compound (6) using oxidizing reagents at −78° C. for a period of 1 to 2 hrs to obtain the aldehyde in situ, treating the aldehyde with a phosphorus ylide at room temperature for a period of 18 to 24 hrs to obtain (5S)-trans-5,6-dihydroxy-2-hexenoate 5,6-acetonide of formula (7)

v) treating compound (7) with osmium tetraoxide and a chiral ligand at 0° C. for a period of 12 to 24 hrs to obtain (2S,3R,5S)-ethyl-trans-2,3,5,6-tetrahydroxy-hexenoate 5,6-acetonide of formula (8)

vi) treating compound (8) with a halide of sulphuryl or thionyl reagent at 0° C. for a period of 30 to 40 mins to obtain (4R)-carbethoxy-(5S)-di-O-isopropylidine propyl-1,3,2-oxathiolane-2-oxide of formula (9)

vii) reacting the compound (9) with a hydride based reagent at room temperature in inert atmosphere for a period of 8 to 12 hrs, hydrolyzing the reaction mixture with a mineral acid to obtain the product of formula (1)

In one of the embodiments of the present invention the mineral acid used in (i) and (vii) may be sulphuric, hydrochloric, toluene sulphonic or trifluoroacetic acid, preferably hydrochloric acid.

In another embodiment the alcohol used in (i) may be alkyl alcohols exemplified by methanol, ethanol, iso-propanol, butanol preferably methanol.

In still another embodiment the reducing agent used in (ii) and (vii) may be hydrides of alkali metals exemplified by sodium borohydride, lithium borohydride, sodium cyanoborohydride and lithium aluminum hydride preferably lithium aluminum hydride/sodium borohydride.

In yet another embodiment the protecting reagent in (iii) may be acetone, 3-pentanone, 2,2-dimethoxy propane and cyclohexanone preferably 2,2-dimethoxy propane.

In another embodiment the oxidizing agent used in (iv) may be an oxidizing agent conventionally used for oxidizing an alcohol to aldehyde such as mixture of oxalyl chloride and dimethyl sulphoxide (DMSO), phosphorus pentoxide and DMSO, pyridinium chlorochromate, pyridinium dichromate and manganese dioxide, preferably mixture of oxalyl chloride and DMSO.

In still another embodiment the phosphorus ylide used in (iv) may be (ethoxycarbonylmethylene)

triphenylphosphorane, trimethyl phosphonoacetate, triethyl phosphonoacetate, ethyl-dimethyl phosphonoacetate, preferably (ethoxycarbonylmethylene)triphenylphosphorane.

In yet another embodiment the chiral ligands may be one of the $1^{st}$ or $2^{nd}$ generation mono- or bidentate ligands such as phthalazine, pyrimidine, phenanthryl, quinoxaline, p-chlorobenzoate, preferably phthalazine.

The invention also resides in the novel intermediates used in the process.

One of the novel intermediate is (2S,3R,5S)-ethyl-trans-2,3,5,6-tetrahydroxy-hexanoate 5,6-acetonide having of formula (8)

FORMULA-8

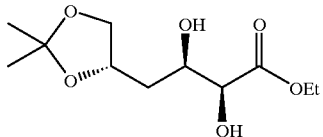

the other novel intermediate is (4R)-carbethoxy-(5S)-di-O-isopropylidine propyl-1,3,2-oxathiolane-2-oxide having of formula

FORMULA-9

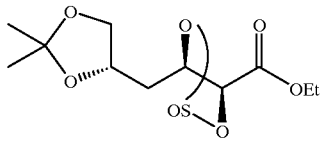

In a feature of the present invention, in order to make all possible stereoisomers of 6-hydroxymethyl-4-hydroxy-o-lactone, a variety of ligands used in the Sharpless asymmetric dihydroxylation procedure were procured from Aldrich Co.

The process of the present invention is further illustrated by the following examples, which may not however be construed to limit the scope of the present invention.

EXAMPLE 1

(S)-malic acid was dissolved in 5% HCl in MeOH and stirred at room temperature for 24 h. The reaction mixture was concentrated and distilled to give (S)-dimethyl malate as colorless liquid. The residual material in the distillation flask was dissolved in 5% HCl in MeOH and processed as above. Distillation afforded additional diester, raising the total yield.

To a stirred suspension of $LiAlH_4$ in dry THF at 0° C. was added a solution of (S)-dimethyl malate in dry THF. The ice bath was removed and the reaction mixture was refluxed for 12 h. Excess $LiAlH_4$ was destroyed by adding water. The white precipitate obtained was filtered and washed with MeOH. The combined filtrate was concentrated to near dryness. The inorganic materials contained in the residual oil were remove by short column chromatography over silica gel. Elution with $CHCl_3$:EtOH (3:1, v/v) then (2:1, v/v) and concentration of the solvents gave (S)-1,2,4-butanetriol as a syrupy liquid.

To a solution of (S)-1,2,4-butanetriol in dry acetone was added 2,2-dimethoxy propane and PTSA (cat). The reaction mixture was stirred at room temperature for 48 h. A pinch of $NaHCO_3$ was added and stirred for 15 min. The reaction mixture was passed through a pad of silica gel. The filtrate was concentrated and distilled (bath temp. 120–125° C./10 mm) to give (S)-1,2,4-butanetriol-1,2-acetonide (6.15 g, 88%) as a colorless liquid.

To a solution of oxalyl chloride in $CH_2Cl_2$ at −78° C. was added dropwise dry DMSO in $CH_2Cl_2$. After 20 min of addition, (S)-1,2,4-butanetriol 1,2-acetonide $CH_2Cl_2$ was added dropwise over 30 min giving a copius white precipitate. After stirring for 1 h at −60° C., $Et_3N$ was added slowly and stirred for 1 h allowing the reaction mixture to warm to room temperature. The reaction mixture was poured into 2N HCl and the organic layer was separated. The aqueous layer was extracted with $CH_2Cl_2$. The combined organic layers were washed with saturated aqueous $NaHCO_3$, brine, dried ($Na_2SO_4$) and passed through a short pad of silica gel. The filtrate was concentrated to give the aldehyde as a pale yellow oil. This was used without further purification.

To a solution of (ethoxycarbonylmethylene) triphenylphosphorane in dry THF was added a solution of the aldehyde in THF at 0° C. The ice-bath was removed and the reaction mixture was stirred for 24 h at room temperature and then concentrated to a thick syrup. Column chromatography of the crude product on silica gel using petroleum ether:EtOAc (95:5) as eluent gave (5S)-Ethyl-trans-5,6-dihydroxy-2-hexenoate 5,6-acetonide as a pale yellow oil.

To a mixture of $K_3Fe(CN)_6$, $K_2CO_3$ and $(DHQD)_2$-PHAL in t-BuOH-$H_2O$ (1:1) cooled at 0° C. was added $OsO_4$ (0.1 M soln. in toluene) followed by methanesulfonamide. After stirring for 5 min at 0° C., the olefin (5S)-ethyl-trans-5,6-dihydroxy-2-hexenoate 5,6-acetonide was added in one portion. The reaction mixture was stirred at 0° C. for 24 h and then quenched with solid sodium sulfite. The stirring was continued for 45 min and the solution was extracted with EtOAc. The combined organic phases were washed with 10% KOH, dried ($Na_2SO_4$) and concentrated. Silica gel column chromatography of the crude product using petroleum ether:EtOAc (3:2) as eluent gave (2S,3R,5S)-ethyl-trans-2,3,5,6-tetrahydroxy-hexanoate 5,6-acetonide as a colorless syrupy liquid.

To a stirred ice-cooled solution of (2S,3R,5S)-ethyl-trans-2,3,5,6-tetrahydroxy-hexanoate 5,6-acetonide in dry $CH_2Cl_2$ was added $Et_3N$ followed by a solution of $SOCl_2$ in dry $CH_2Cl_2$ over 5 min. The reaction mixture was stirred for 30 min and then quenched by addition of $H_2O$ and $CH_2Cl_2$. The organic layer was separated and washed with brine, dried ($Na_2SO_4$) and passed through a pad of neutral alumina. The filtrate was concentrated to give a yellow liquid. Column chromatography of the crude product on silica gel column using petroleum ether:EtOAc (95:5) as eluent gave (4R)-carbethoxy-(5S)-di-O-isopropylidine propyl-1,3,2-oxathiolane-2-oxide as a pale yellow oil.

To a solution of cyclic sulfite in dry THF was added $NaBH_4$, under argon. The reaction mixture was stirred under argon at room temperature for 12 h. The solvent was removed under reduced pressure and MeOH was added to the residue. The reaction mixture was acidified with 4N $H_2SO_4$ and stirred at room temperature overnight. The solvent was stripped off under reduced pressure and the residue was purified by silica gel column chromatography using petroleum ether:EtOAc (1:4) as eluent to give the lactone (4R,6S)4-hydroxy-6-hydroxymethyl-tetrahydro-pyran-2-one (1) as a colorless oil.

EXAMPLE 2

(S)-malic acid was dissolved in 5% $H_2SO_4$ in EtOH and stirred at room temperature for 24 h. The reaction mixture was concentrated and distilled to give (S)-diethyl malate as colorless liquid. The residual material in the distillation flask was dissolved in 5% H$_2$SO$_4$ in EtOH and processed as above. Distillation afforded additional diester, raising the total yield.

To a stirred suspension of LiAlH$_4$ in dry-THF at 0° C. was added a solution of (S)-diethyl malate in dry THF. The ice bath was removed and the reaction mixture was refluxed for 12 h. Excess LiAlH$_4$ was destroyed by adding water. The white precipitate obtained was filtered and washed with MeOH. The combined filtrate was concentrated to near dryness. The inorganic materials contained in the residual oil were removed by short column chromatography over silica gel. Elution with CHCl$_3$:EtOH (3:1, v/v) then (2:1, v/v) and concentration of the solvents gave (S)-1,2,4-butanetriol as a syrupy liquid.

To a solution of (S)-1,2,4-butanetriol in dry acetone was added 2,2-dimethoxy propane and PTSA (cat). The reaction mixture was stirred at room temperature for 48 h. A pinch of NaHCO$_3$ was added and stirred for 15 min. The reaction mixture was passed through a pad of silica gel. The filtrate was concentrated and distilled to give (S)-1,2,4-butanetriol 1,2-acetonide as a colorless liquid.

To a suspension of Phosphorus pentoxide in CH$_2$Cl$_2$ at 0° C. was added dropwise dry DMSO in CH$_2$Cl$_2$. After 20 min of addition, (S)-1,2,4-butanetriol 1,2-acetonide CH$_2$Cl$_2$ was added dropwise over 30 min giving a copius white precipitate. After stirring for 1 h at 0° C., Et$_3$N was added slowly and stirred for 1 h allowing the reaction mixture to warm to room temperature. The reaction mixture was poured into 2N HCl and the organic layer was separated. The aqueous layer was extracted with CH$_2$Cl$_2$. The combined organic layers were washed with saturated aqueous NaHCO$_3$, brine, dried (Na$_2$SO$_4$) and passed through a short pad of silica gel. The filtrate was concentrated to give the aldehyde as a pale yellow oil. This was used without further purification.

To a suspension of the ylide generated from triethyl phosphonoacetate and NaH in dry THF was added a solution of the aldehyde in THF at 0° C. The ice-bath was removed and the reaction mixture was stirred for 24 h at room temperature and then diluted with water and extracted with EtOAc. The combined organic extracts were washed with water, brine, dried (Na$_2$SO$_4$) and concentrated to a thick syrup. Column chromatography of the crude product on silica gel using petroleum ether:EtOAc (95:5) as eluent gave (5S)-Ethyl-trans-5,6-dihydroxy-2-hexenoate 5,6-acetonide as a pale yellow oil.

To a mixture of K$_3$Fe(CN)$_6$, K$_2$CO$_3$ and (DHQD)$_2$-PHAL in t-BuOH-H$_2$O (1:1) cooled at 0° C. was added OsO$_4$ (0.1 M soln. in toluene) followed by methanesulfonamide. After stirring for 5 min at 0° C., the olefin (5S)-ethyl-trans-5,6-dihydroxy-2-hexenoate 5,6-acetonide was added in one portion. The reaction mixture was stirred at 0° C. for 24 h and then quenched with solid sodium sulfite. The stirring was continued for 45 min and the solution was extracted with EtOAc. The combined organic phases were washed with 10% KOH, dried (Na$_2$SO$_4$) and concentrated. Silica gel column chromatography of the crude product using petroleum ether:EtOAc (3:2) as eluent gave (2S,3R,5S)-ethyl-trans-2,3,5,6-tetrahydroxy-hexanoate 5,6-acetonide as a colorless syrupy liquid.

To a stirred ice-cooled solution of (2S,3R,5S)-ethyl-trans-2,3,5,6-tetrahydroxy-hexanoate 5,6-acetonide in dry CH$_2$Cl$_2$ was added pyridine followed by a solution of SOCl$_2$ in dry CH$_2$Cl$_2$ over 5 min. The reaction mixture was stirred for 30 min and then quenched by addition of H$_2$O and CH$_2$Cl$_2$. The organic layer was separated and washed with brine, dried (Na$_2$SO$_4$) and passed through a pad of neutral alumina. The filtrate was concentrated to give a yellow liquid. Column chromatography of the crude product on silica gel column using petroleum ether:EtOAc (95:5) as eluent gave (4R)-carbethoxy-(5S)-di-O-isopropylidine propyl-1,3,2-oxathiolane-2-oxide as a pale yellow oil.

To a solution of cyclic sulfite in dry THF was added NaCNBH$_4$, under argon. The reaction mixture was stirred under argon at room temperature for 12 h. The solvent was removed under reduced pressure and MeOH was added to the residue. The reaction mixture was acidified with 4N HCl and stirred at room temperature overnight. The solvent was stripped off under reduced pressure and the residue was purified by silica gel column chromatography using petroleum ether:EtOAc (1:4) as eluent to give the lactone (4R, 6S)-4-hydroxy-6-hydroxymethyl-tetrahydro-pyran-2-one (1) as a colorless oil.

EXAMPLE 3

(S)-malic acid was dissolved in isopropanol and p-toluenesulphonic acid (cat) was added and stirred at room temperature for 24 h. The reaction mixture was concentrated and distilled to give (S)-diisopropyl malate as colorless liquid. The residual material in the distillation flask was dissolved in EtOH and processed as above. Distillation afforded additional diester, raising the total yield.

To a stirred suspension of NaBH$_4$ in dry THF at 0° C. was added a solution of (S)-diisopropyl malate in dry THF. The ice bath was removed and the reaction mixture was refluxed for 12 h. Excess NaBH$_4$ was destroyed by adding water. The white precipitate obtained was filtered and washed with MeOH. The combined filtrate was concentrated to near dryness. The inorganic materials contained in the residual oil were removed by short column chromatography over silica gel. Elution with CHCl$_3$:EtOH (3:1, v/v) then (2:1, v/v) and concentration of the solvents gave (S)-1,2,4-butanetriol as a syrupy liquid.

To a solution of (S)-1,2,4-butanetriol in dry acetone was added PTSA (cat). The reaction mixture was stirred at room temperature for 48 h. A pinch of NaHCO$_3$ was added and stirred for 15 min. The reaction mixture was passed through a pad of silica gel. The filtrate was concentrated and distilled to give (S)-1,2,4-butanetriol 1,2-acetonide as a colorless liquid.

To a suspension of pyridinium chlorochromate and sodium acetate in CH$_2$Cl$_2$ at 0° C. was added dropwise (S)-1,2,4-butanetriol 1,2-acetonide in CH$_2$Cl$_2$. After stirring for 4 h at 0° C. the reaction mixture was warmed to room temperature and diluted with ether and filtered. The filtrate was concentrated to give the aldehyde as a pale yellow oil. This was used without further purification.

To a suspension of the ylide generated from trimethyl phosphonoacetate and NaH in dry THF was added a solution of the aldehyde in THF at 0° C. The ice-bath was removed and the reaction mixture was stirred for 24 h at room temperature and then diluted with water and extracted with EtOAc. The combined organic extracts were washed with water, brine, dried (Na$_2$SO$_4$) and concentrated to a thick syrup. Column chromatography of the crude product on silica gel using petroleum ether:EtOAc (95:5) as eluent gave (5S)-Ethyl-trans-5,6-dihydroxy-2-hexenoate 5,6-acetonide as a pale yellow oil.

To a mixture of K$_3$Fe(CN)$_6$, K$_2$CO$_3$ and (DHQD)$_2$-PHAL in t-BuOH-H$_2$O (1:1) cooled at 0° C. was added OsO$_4$ (0.1 M soln. in toluene) followed by methanesulfonamide. After stirring for 5 min at 0° C., the olefin (5S)-ethyl-trans-5,6-dihydroxy-2-hexenoate 5,6-acetonide was added in one portion. The reaction mixture was stirred at 0° C. for 24 h and then quenched with solid sodium sulfite. The stirring was continued for 45 min and the solution was extracted with EtOAc. The combined organic phases were washed with 10% KOH, dried (Na₂SO₄) and concentrated. Silica gel column chromatography of the crude product using petroleum ether:EtOAc (3:2) as eluent gave (2S,3R,5S)-ethyl-trans-2,3,5,6-tetrahydroxy-hexanoate 5,6-acetonide as a colorless syrupy liquid.

To a stirred ice-cooled solution of (2S,3R,5S)-ethyl-trans-2,3,5,6-tetrahydroxy-hexanoate 5,6-acetonide in dry CH₂Cl₂ was added pyridine followed by a solution of SOCl₂ in dry CH₂Cl₂ over 5 min. The reaction mixture was stirred for 30 min and then quenched by addition of H₂O and CH₂Cl₂. The organic layer was separated and washed with brine, dried (Na₂SO₄) and passed through a pad of neutral alumina. The filtrate was concentrated to give a yellow liquid. Column chromatography of the crude product on silica gel column using petroleum ether:EtOAc (95:5) as eluent gave (4R)-carbethoxy-(5S)-di-O-isopropylidine propyl-1,3,2-oxathiolane-2-oxide as a pale yellow oil.

To a solution of cyclic sulfite in dry THF was added LiBH4, under argon. The reaction mixture was stirred under argon at room temperature for 12 h. The solvent was removed under reduced pressure and MeOH was added to the residue. The reaction mixture was acidified with 4N HCl and stirred at room temperature overnight. The solvent was stripped off under reduced pressure and the residue was purified by silica gel column chromatography using petroleum ether:EtOAc (1:4) as eluent to give the lactone (4R, 6S)4-hydroxy-6-hydroxymethyl-tetrahydro-pyran-2-one (1) as a colorless oil.

Advantages of the present invention are:

i) The process relatively involves less number of steps.

ii) The reactions involved in each step, according to the present invention, could be carried out relatively at lower temperature or room temperature.

iii) The process leads to high yields of the desired products.

iv) All possible stereoisomers of the desired lactone could be prepared using this process.

v) The process gives high enantio-and diastereoselectivity of the products.

vi) The chiral ligands used to induce chirality could be recovered.

We claim:

1. An improved process for the synthesis of (4R,6S)-4-hydroxy-6-hydroxymethyl tetrahydro-pyran-2-one which comprises i) reacting the (s)-(−)-Malic acid with a mixture of mineral acid and alcohol at room temperature for a period of 18 to 30 hrs to obtain the diester of (S)-(−) Malic acid of formula (4)

FORMULA-4

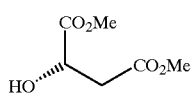

ii) reducing the compound (4) with a hydride reducing reagent at room temperature to reflux temperature for a period of 8 to 12 hrs to obtain (S)-1,2,4-butanetriol of formula (5)

FORMULA-5

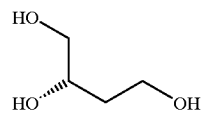

iii) treating the compound (5) with protecting reagent at room temperature for a period of 36 to 48 hrs to obtain (S)-1,2,4-butanetriol 1,2-acetonide of formula (6)

FORMULA-6

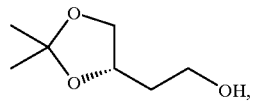

iv) oxidizing compound (6) using oxidizing reagents at −78° C. for a period of 1 to 2 hrs to obtain the aldehyde in situ, treating the aldehyde with a phosphorous ylide at room temperature for a period of 18 to 24 hrs to obtain (5S)-trans-5,6-dihydroxy-2-hexenoate 5,6-acetonide of formula (7)

FORMULA-7

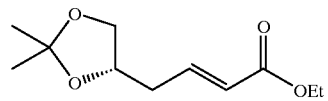

v) treating compound (7) with osmium tetraoxide and a chiral ligand at 0° C. for a period of 12 to 24 hrs to obtain (2S,3R,5S)-ethyl-trans-2,3,5,6-tetrahydroxy-hexanoate 5,6-acetonide of formula (8)

FORMULA-8

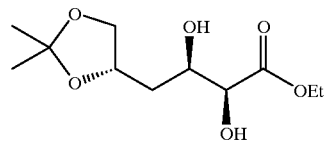

vi) treating compound (8) with a halide of sulphuryl or thionyl reagent at 0° C. for a period of 30 to 40 mins to obtain (4R)-carbethoxy-(5S)-di-O-isopropylidine propyl-1,3,2-oxathiolane-2-oxide of formula (9)

FORMULA-9

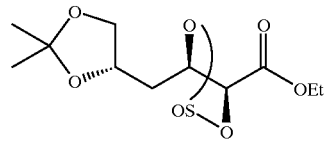

vii) reacting the compound (9) with a hydride based reagent at room temperature in inert atmosphere for a period of 8 to 12 hrs, hydrolyzing the reaction mixture with a mineral acid to obtain the product of formula (1)

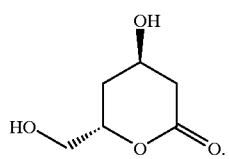

FORMULA-1

2. A process as claimed in claim 1 wherein the mineral acid used in (i) and (vii) is sulphuric, hydrochloric, toluene sulphonic acid or a trifluoroacetic acid preferably hydrochloric acid.

3. A process as claimed in claim 1 wherein the alcohol used in (i) is an alkyl alcohols exemplified by methanol, ethanol, iso-propanol, butanol preferably methanol.

4. A process as claimed in claim 1 wherein the reducing agent used in (ii) and (vii) are hydrides of alkali metals exemplified by sodium borohydride, lithium borohydride, sodium cyanoborohydride and lithium aluminum hydride preferably lithium aluminum hydride/sodium borohydride.

5. A process as claimed in claim 1 wherein the protecting reagent in (iii) is acetone, 3-pentanone, 2-2 dimethoxy propane and cyclohexanone preferably 2-2-dimethoxy propane.

6. A process as claimed in claim 1 wherein the oxidizing agent used in (iv) is an oxidizing agent conventionally used for oxidizing an alcohol to aldehyde such as mixture of oxalyl chloride and Dimethyl sulphoxide (DMSO), phosphorus pentoxide and DMSO, pyridinium chlorochromate, pyridinium dichromate and manganese dioxide, preferably mixture of oxalyl chloride and DMSO.

7. A process as claimed in claim 1 wherein the phosphorus ylide used in (iv) is (ethoxycarbonylmethylene) triphenylphosphorane, trimethyl phosphono acetate, triethyl phosphonoacetate, ethyl dimethyl phosphono acetate, preferably (ethoxycarbonylmethylene)triphenylphosphorane.

8. A process as claimed in claim 1 wherein the chiral ligands used are one of the $1^{st}$ or $2^{nd}$ generation mono- or bidentate ligands such as phthalazine, pyrimidine, phenanthryl, quinoxaline, p-chlorobenzoate, preferably phthalazine.

9. A novel intermediate (2S,3R,5S)-ethyl-trans-2,3,5,6-tetrahydroxy-hexanoate 5,6-acetonide having of formula (8)

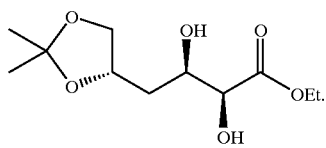

FORMULA-8

10. A novel intermediate (4R)-carbethoxy-(5S)-di-O-isopropylidine propyl-1,3,2-oxathiolane-2-oxide having of formula (9)

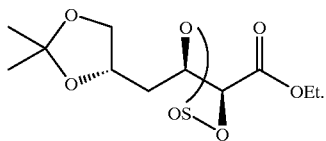

FORMULA-9

* * * * *